United States Patent
Ikemoto

(10) Patent No.: US 11,021,476 B2
(45) Date of Patent: Jun. 1, 2021

(54) PYRROLOQUINOLINE QUINONE MONOSODIUM AND METHOD FOR PRODUCING THE SAME, AND COMPOSITION COMPRISING THE SAME

(71) Applicant: Mitsubishi Gas Chemical Company, Inc., Chiyoda-ku (JP)

(72) Inventor: Kazuto Ikemoto, Niigata (JP)

(73) Assignee: Mitsubishi Gas Chemical Company, Inc., Chiyoda-ku (JP)

( * ) Notice: Subject to any disclaimer, the term of this patent is extended or adjusted under 35 U.S.C. 154(b) by 0 days.

(21) Appl. No.: 16/309,179

(22) PCT Filed: Jun. 15, 2017

(86) PCT No.: PCT/JP2017/022206
§ 371 (c)(1),
(2) Date: Dec. 12, 2018

(87) PCT Pub. No.: WO2018/003531
PCT Pub. Date: Jan. 4, 2018

(65) Prior Publication Data
US 2019/0330205 A1    Oct. 31, 2019

(30) Foreign Application Priority Data
Jun. 29, 2016    (JP) .............................. JP2016-128941

(51) Int. Cl.
| C07D 471/04 | (2006.01) |
| A23L 33/10 | (2016.01) |
| A23F 3/30 | (2006.01) |
| A61K 8/49 | (2006.01) |
| A61Q 19/00 | (2006.01) |

(52) U.S. Cl.
CPC .............. *C07D 471/04* (2013.01); *A23F 3/30* (2013.01); *A23L 33/10* (2016.08); *A61K 8/4926* (2013.01); *A61Q 19/00* (2013.01); *A23V 2002/00* (2013.01); *C07B 2200/13* (2013.01)

(58) Field of Classification Search
CPC .................................................. C07D 471/04
USPC ........................................................ 546/84
See application file for complete search history.

(56) References Cited

U.S. PATENT DOCUMENTS

| 9,163,014 B2 * | 10/2015 | Edahiro | ............... | C07D 471/04 |
| 10,364,244 B2 * | 7/2019 | Yang | ..................... | A61Q 19/00 |

| 2012/0116087 A1 | 5/2012 | Edahiro et al. |
| 2012/0226045 A1 | 9/2012 | Ikemoto et al. |
| 2016/0039816 A1 | 2/2016 | Edahiro et al. |

FOREIGN PATENT DOCUMENTS

| CN | 101885725 A | 11/2010 |
| CN | 108026091 A | 5/2018 |
| EP | 2 455 379 A1 | 5/2012 |
| EP | 2 497 769 A1 | 9/2012 |
| JP | 62-246575 A | 10/1987 |
| JP | 2013-112677 A | 6/2013 |
| WO | WO 2011/007633 A1 | 1/2011 |
| WO | WO 2011/055796 A1 | 5/2011 |
| WO | WO 2012/173217 A | 12/2012 |
| WO | WO 2013/051414 A | 4/2013 |
| WO | WO 2014/027669 A | 12/2014 |
| WO | WO 2017050171 | * 3/2017 ................ A61P 9/10 |

OTHER PUBLICATIONS

Kazuto Ikemoto et al; "Unusual Ionic Bond and Solubility Mechanism of NanPQQ (n=0-4) Crystals"; Cryst. Growth Des., 4118-4123, Jul. 3, 2017 American Chemical Society.
International Search Report dated Aug. 15, 2017 in PCT/JP2017/022206 filed Jun. 15, 2017.
Ishida, T. et al., "Molecular and Crystal Structure of PQQ (Methoxatin), a Novel Coenzyme of Quinoproteins: Extensive Stacking Character and Metal Ion Interaction," Journal of American Chemical Society, 1989, vol. 111, pp. 6822-6828.
Ikemoto, K. et al., "Crystal structure and characterization of pyrroloquinoline quinone disodium trihydrate," Chemistry Central Journal, 2012, 6:57 doi: 10.1186/1752-153X-6-57, 7 pages.
Teisuke Okano. "Shin Yakuzaigakusouron", Apr. 10, 1987, p. 111.
Office Action dated Mar. 19, 2021 in counterpart Japanese Patent Application No. 2018-525047, 7 pages.

* cited by examiner

*Primary Examiner* — Nizal S Chandrakumar
(74) *Attorney, Agent, or Firm* — Oblon, McClelland, Maier & Neustadt, L.L.P.

(57) ABSTRACT

The present invention provides pyrroloquinoline quinone monosodium having a structure represented by the following formula (1).

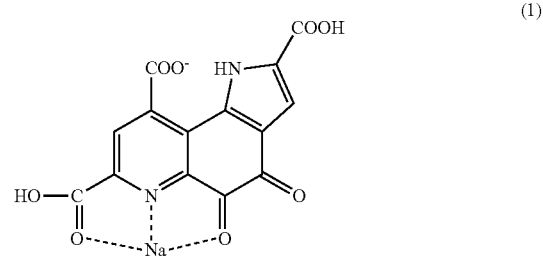

(1)

2 Claims, 6 Drawing Sheets

[Figure 9]
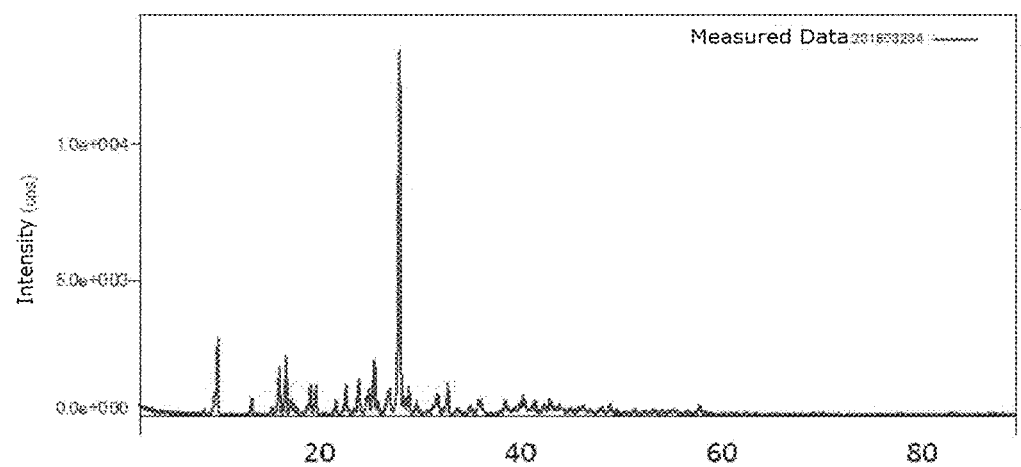
[Figure 10]
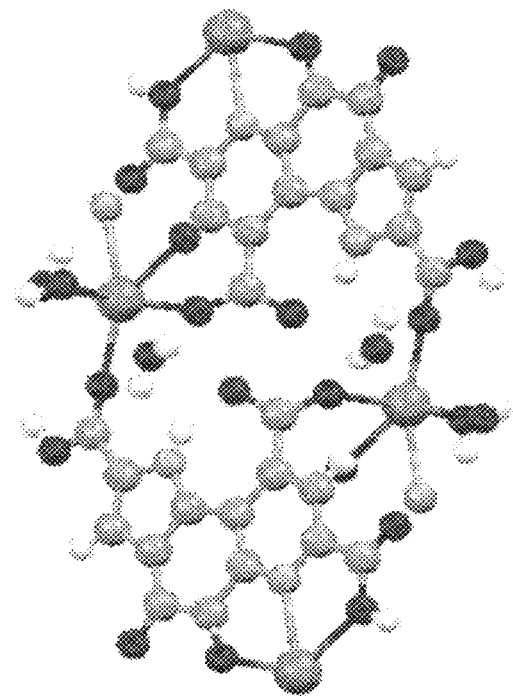

PYRROLOQUINOLINE QUINONE MONOSODIUM AND METHOD FOR PRODUCING THE SAME, AND COMPOSITION COMPRISING THE SAME

TECHNICAL FIELD

The present invention relates to pyrroloquinoline quinone monosodium and a method for producing the same, and a composition comprising the same.

BACKGROUND ART

Pyrroloquinoline quinone (hereinafter sometimes simply referred to as "PQQ") is present not only in bacteria but in mold and yeast, eukaryotes, and serves an important function as a coenzyme, and many physiological activities such as cell multiplication promotion action, anticataract action, liver disease preventive treatment action, wound healing action, antiallergic action, reverse transcriptase inhibition action, and glyoxalase I inhibition action-anticancer action have been clarified by recent years. Therefore, PQQ attracts attention as a substance useful in the fields of drugs, foods, and cosmetics. For example, in the field of drugs, applications of PQQ as therapeutic drugs for the heart, the skin, nerves, and the like are expected. In the field of cosmetics, applications of PQQ as a substance having a beautiful skin effect are expected.

Pyrroloquinoline quinone is formed in culture, and the production step is performed in an aqueous solution, and therefore, usually, pyrroloquinoline quinone is obtained in the form of an alkali metal salt. Pyrroloquinoline quinone is known to be water-soluble, but PQQ having a free form structure exhibits low water solubility, and actually, the water solubility improves by forming an alkali metal salt of PQQ. Particularly a sodium salt of PQQ has no toxicity and is therefore easy to use. Actually, a disodium salt of PQQ is approved as a food and used. For crystals of a disodium salt of PQQ, hydrated crystals are known (for example, see Patent Literature 1 and Non Patent Literatures 1 and 2)

A pyrroloquinoline quinone monosodium salt represented by the following structural formula differs greatly in solubility compared with the disodium salt and is therefore suitable for use for a different purpose of use. For example, it is suitable when slow dissolution in water is desired.

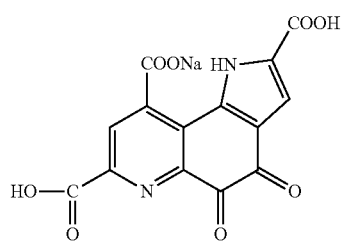

As a method for synthesizing a monosodium salt having a structure in which hydrogen in one place in the carboxylic acid of pyrroloquinoline quinone is replaced by sodium, a method of dissolving PQQ in tetrahydrofuran and reacting it with sodium hydroxide in an aqueous solution is proposed (for example, see Patent Literature 2).

CITATION LIST

Patent Literature

Patent Literature 1: International Publication No. WO 2011/007633

Patent Literature 2: Chinese Laid-Open Application Publication No. 101885725

Non Patent Literature

Non Patent Literature 1: Ishida, T. et al., "Molecular and crystal structure of PQQ (methoxatin), a novel coenzyme of quinoproteins: extensive stacking character and metal ion interaction", Journal of American Chemical Society, 1998, Vol. 111, p. 6822-6828

Non Patent Literature 2: Ikemoto, K. et al., Crystal structure and characterization of pyrroloquinoline quinone disodium trihydrate, Chemistry Central Journal 2012, 6:57 doi:10.1186/1752-153X-6-57

SUMMARY OF INVENTION

Technical Problem

However, tetrahydrofuran used in the method described in Patent Literature 2 has inflammability and is not a solvent that can be used for a food. In addition, when pyrroloquinoline quinone is produced from culture in the method for producing a sodium salt described in Patent Literature 2, a solution containing pyrroloquinoline quinone cultured under neutral conditions has a structure having a counterion. Therefore, pyrroloquinoline quinone needs to be converted into a free form under acidic conditions for further neutralization. In addition, the obtained substance has a fibrous state structure, has high bulk, and is poor in fluidity. Therefore, a disadvantage is that the content at the same volume decreases. In addition, the fibrous crystals are poor in fluidity and difficult to handle in a solid state.

It is known that the stability, handling, and color of a pyrroloquinoline quinone sodium salt change by a different sodium bonding place and crystal structure. Regarding the handling, a fibrous solid is likely to be in the form of a film when filtered, poor in fluidity in handling as a powder, and difficult to use. In order to improve this, the operation of grinding the state of hardening in the form of a film is necessary. Such an operation is different from the way of forming crystals that has been known so far, and therefore it is relatively difficult to obtain stable crystals, and stable crystals and a method for producing the same are required. In order to obtain stable crystals, particularly it is important to increase bulk density. Thus, the improvement of fluidity can also be promoted.

In applying a compound having the structure of PQQ to a food or a cosmetic, for the compound having the structure of PQQ, one that is water-soluble and less likely to change in color and has high crystallinity is required. In addition, a method that allows safe and quick production is required.

Accordingly, the present invention is to provide a method for producing pyrroloquinoline quinone monosodium comprising no fibrous crystal and having high bulk density, without using a harmful organic solvent, and pyrroloquinoline quinone monosodium having a novel structure. Further, it is an object of the present invention to provide a method for quickly producing a pyrroloquinoline quinone monosodium crystal, and a pyrroloquinoline quinone monosodium crystal having a novel structure.

Solution to Problem

The present inventor has found that by preparing PQQ disodium or PQQ trisodium under particular conditions, a PQQ monosodium crystal having a novel structure is obtained. The present inventor has also found that this PQQ monosodium crystal is less likely to change color. The present invention is an invention based on such findings.

In other words, according to the present invention, the following inventions are provided.

[1]

Pyrroloquinoline quinone monosodium having a structure represented by following formula (1).

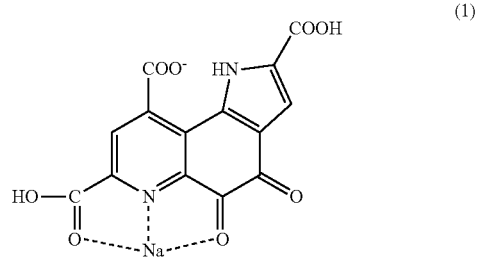

(1)

[2]

The pyrroloquinoline quinone monosodium according to [1], being a crystal and showing 2θ angle peaks at 7.9, 10.9, 11.2, 18.4, 22.4, 25.7, 28.0, and 28.8±0.4° in powder X-ray diffraction using Cu Kα radiation.

[3]

Dipyrroloquinoline quinone monosodium having a structure represented by following formula (2).

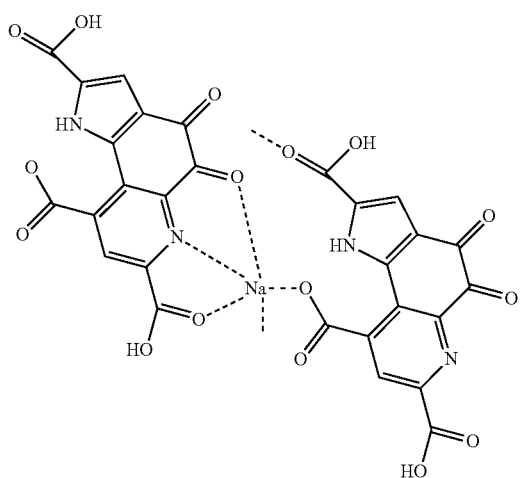

(2)

[4]

The dipyrroloquinoline quinone monosodium according to [3], being a crystal and showing 2θ angle peaks at 9.9, 16.1, 16.8, and 28.1±0.4° in powder X-ray diffraction using Cu Kα radiation.

[5]

A method for producing the pyrroloquinoline quinone monosodium according to [1], comprising a step of bringing pyrroloquinoline quinone disodium and/or pyrroloquinoline quinone trisodium into contact with an excess amount of an acid.

[6]

The method according to [5], wherein the step is performed in presence of common salt.

[7]

The method according to [5] or [6], wherein the step is performed in presence of an aqueous solution having an ethanol concentration of 10 to 90% by mass.

[8]

The method according to any one of [5] to [7], wherein a mixed crystal of pyrroloquinoline quinone disodium and pyrroloquinoline quinone monosodium is obtained in the step.

[9]

A composition comprising both of either the pyrroloquinoline quinone monosodium according to [1] or [2] or the dipyrroloquinoline quinone monosodium according to [3] or [4], and pyrroloquinoline quinone disodium.

Advantageous Effects of Invention

The PQQ monosodium crystal of the present invention not only has high purity but is improved in solubility, dispersibility in a solution, and penetration into the skin, and is useful as a component of a cosmetic, a drug, or a functional food.

BRIEF DESCRIPTION OF DRAWINGS

FIG. 9 shows the powder X-ray diffraction of the PQQ monosodium crystals 2 of Example 7.

FIG. 10 shows a structure showing the PQQ monosodium crystal 2 of Example 7 with balls and sticks.

DESCRIPTION OF EMBODIMENTS

An embodiment of the present invention (hereinafter also described as "this embodiment") will be described in detail below. The following embodiment is an illustration for explaining the present invention, and the present invention is not limited only to the embodiment.

The present inventor has examined the crystal structure of certain PQQ monosodium in order to obtain a crystal having high bulk density, and as a result, the PQQ monosodium has turned out to be a salt having a bond that has not been reported so far. A conventional salt of pyrroloquinoline quinone has a structure in which the hydrogen of a carboxylic acid comes off, and sodium comes in instead. The PQQ monosodium of the present invention is PQQ monosodium having a structure represented by the following formula (1).

The PQQ monosodium in this embodiment has, for example, the structure represented by the following formula (1). For the bonding analysis of these, single crystal structure analysis is necessary. Conventionally, it is thought that in a salt of the carboxylic acid of PQQ, a carboxylic acid from which the acidic hydrogen atom comes off and sodium are bonded to each other. Crystals of pyrroloquinoline quinone that have been reported so far also have a similar tendency. However, the pyrroloquinoline quinone monosodium having the structure represented by the following formula (1) (hereinafter also described as "PQQ monosodium 1") has a structure unexpected from the conventional thought. In the structure of the PQQ monosodium in this embodiment, sodium is bonded to a carboxylic acid which is bonded to a quinoline structure and in which hydrogen remains, a nitrogen atom in the quinoline structure, and an oxygen atom bonded to the quinoline structure, and the hydrogen of a carboxylic acid which is bonded to the quinoline structure and to which sodium is not bonded is dissociated.

Figure 1:
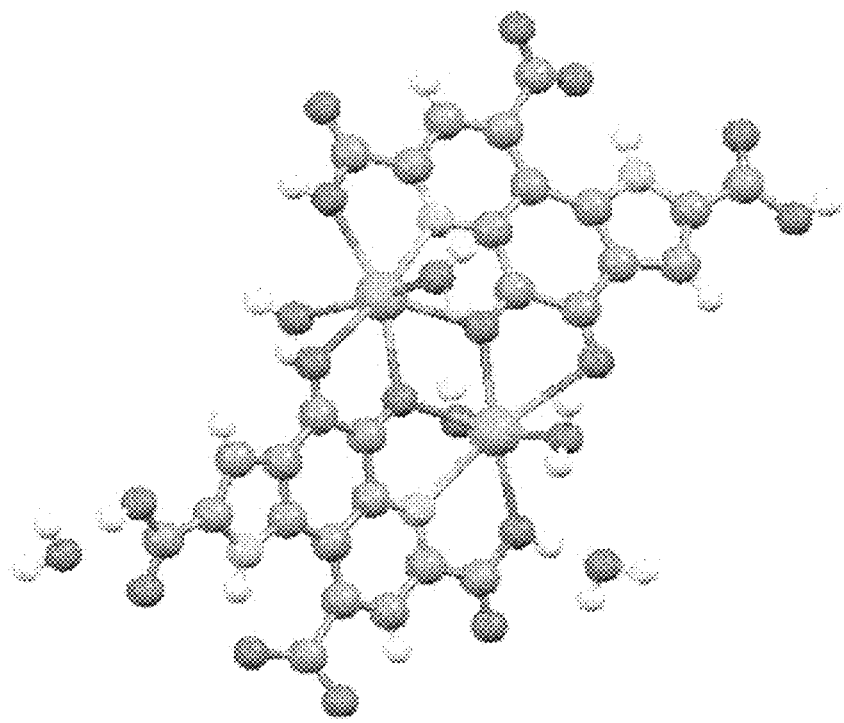
FIG. 1 shows a structure showing the PQQ monosodium crystal of the present invention with balls and sticks.
Figure 2:
FIG. 2 shows a structure showing the PQQ monosodium crystal of the present invention with balls and sticks, seen from a side.

FIG. 1 and FIG. 2 show the crystal structure of the PQQ monosodium 1 in this embodiment with balls and sticks. An actual crystal of the PQQ monosodium 1 in this embodiment has a unit comprising two structures represented by the following formula (1).

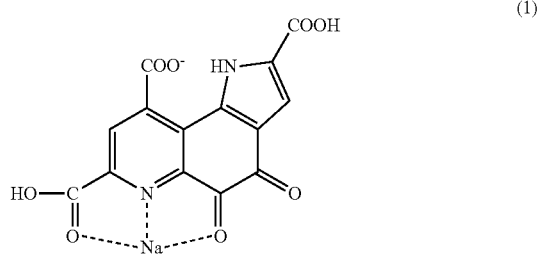

(1)

The PQQ monosodium in this embodiment also has, for example, a structure represented by the following formula (2). Dipyrroloquinoline quinone monosodium having the structure represented by the following formula (2) (hereinafter also described as "PQQ monosodium 2", and simply described as "PQQ monosodium" when not distinguished from the PQQ monosodium 1) also has a structure unexpected from the conventional thought. In the structure of the PQQ monosodium 2 in this embodiment, sodium is bonded to a carboxylic acid which is bonded to a quinoline structure and in which hydrogen remains, a nitrogen atom in the quinoline structure, and an oxygen atom bonded to the quinoline structure, in one molecule of PQQ, and a carboxylic acid which is bonded to a quinoline structure and in which hydrogen does not remain, and a carboxylic acid bonded to a pyrrole structure, in the other molecule of PQQ.

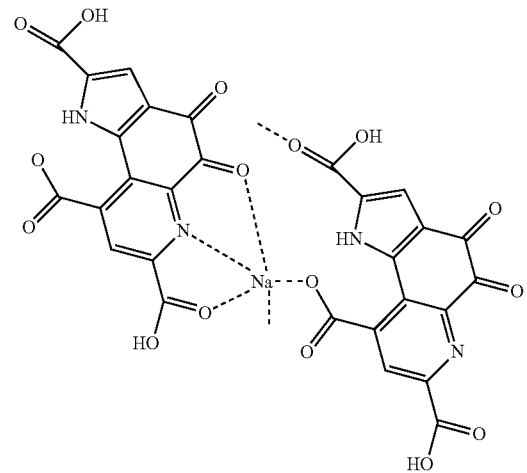

(2)

The crystal of the PQQ monosodium in this embodiment is preferably a hydrated crystal. As a hydrated crystal, for example, the crystal structure of certain PQQ monosodium derived from crystal structure analysis is a structure having two PQQ units and two sodiums. The crystal of the PQQ monosodium in this embodiment is characterized in that an unionized carboxylic acid COOH forms a bond with sodium, unlike sodium salts that have been reported so far. Pyrroloquinoline quinone having such a bond is not known and is a PQQ monosodium crystal having a novel bond.

A crystal that is structure-determined by a single crystal can be identified by conversion from this data into powder X-ray diffraction data. Therefore, the crystal having this structure can be confirmed not only by single crystal structure analysis but by powder X-ray diffraction. The crystal of the PQQ monosodium 1 (hereinafter also described as a "crystal 1") in this embodiment is a PQQ monosodium crystal showing $2\theta$ angle peaks at 7.9, 10.9, 11.2, 18.4, 22.4, 25.7, 28.0, and 28.8±0.4° in powder X-ray diffraction using Cu Kα radiation. These peaks can be observed by a general powder X-ray diffraction apparatus equipped with a monochromator. Since measurement errors are also included in measured data, the crystal defined in this embodiment has a crystal form having rational identity regarding peak angles. The water of crystallization in this crystal 1 is, for example, 9.2% by mass. Actually, the amount of water changes due to the influence of dryness and humidity and may also be 15 to 18% by mass. This crystal form is a quadrangular prism. This crystal form is not fibrous, and thus handling as a powder is easy.

The crystal of the PQQ monosodium 2 (hereinafter also described as a "crystal 2", and simply described as a "crystal" when not distinguished from the crystal 1) in this embodiment is a PQQ monosodium crystal showing $2\theta$ angle peaks at 9.9, 16.1, 16.8, and 28.1±0.4° in powder X-ray diffraction using Cu Kα radiation. This crystal is a crystal in which the crystal form 1 is further stabilized. The amount of water in this crystal 2 is small. The amount of water in the crystal 2 is, for example, 4 to 7% by mass. Pyrroloquinoline quinone monosodium containing a small amount of water is more hydrophobic and has the merit of improving affinity for oil. An actual crystal may also be obtained in a state in which the crystal 1 and the crystal 2 are mixed.

The method for producing pyrroloquinoline quinone monosodium in this embodiment comprises the step of bringing pyrroloquinoline quinone disodium and/or pyrroloquinoline quinone trisodium into contact with an acid. The acid is preferably an excess amount of the acid. By contact with the excess amount of the acid, production can be quickly performed. Here, the excess amount of the acid means that the amount of the acid is preferably 2 to 200 times, more preferably 3 to 100 times, and further preferably 5 to 50 times that of pyrroloquinoline quinone disodium and/or pyrroloquinoline quinone trisodium. Here, "bringing" means that at least parts of pyrroloquinoline quinone disodium and/or pyrroloquinoline quinone trisodium and the acid are in contact with each other, and includes adding the acid to pyrroloquinoline quinone disodium and/or pyrroloquinoline quinone trisodium, and mixing pyrroloquinoline quinone disodium and/or pyrroloquinoline quinone trisodium and the acid.

Crystals of PQQ monosodium obtained by the production method in this embodiment are preferably dried and used. Specifically, the drying of the crystals can be performed by freeze drying, atmospheric pressure drying, or reduced pressure drying. The drying temperature differs depending on the method and can be, for example, −80 to 250° C., preferably, −60 to 250° C. The lower limit of the drying temperature is starting temperature in freeze drying, and the upper limit is a temperature at which the decomposition of the crystals does not occur. For example, the drying temperature can be −80 to 0° C., preferably −60 to 0° C., in freeze drying, 40 to 250° C. in atmospheric pressure drying, and 0 to 250° C. in reduced pressure drying.

The production method in this embodiment is characterized by removing a sodium ion from pyrroloquinoline quinone disodium and pyrroloquinoline quinone trisodium. By adding an acid, the sodium ion is removed as the sodium salt of the acid. By using an excess amount of an acid, crystallization at high speed is possible, and at this time, the sodium ion is preferably allowed to coexist. Specifically, the sodium salt is sodium chloride in the case of hydrochloric acid and sodium sulfate for sulfuric acid. Pyrroloquinoline quinone monosodium has low solubility, and the sodium salt to be removed has high solubility and is therefore separated.

The crystals 1 of PQQ monosodium in this embodiment are produced, for example, by suspending or dissolving PQQ disodium or PQQ trisodium in water or ethanol-water and adding an acid. The crystals 1 are produced in the step of reacting PQQ disodium or PQQ trisodium with an acid in water or ethanol-water. When PQQ trisodium is used as a raw material, the PQQ monosodium in this embodiment can be crystallized by adding PQQ trisodium to an aqueous solution having an ethanol concentration of 0 to 90% by mass, and then adding an acid to adjust the pH of the aqueous solution in the range of 0 to 2. When PQQ disodium is used as a raw material, the PQQ monosodium in this embodiment can be crystallized by adding PQQ disodium to an aqueous solution having an ethanol concentration of 0 to 90% by mass, and then adding an acid to adjust the pH of the aqueous solution in the range of 0 to 2. For more detailed description, when PQQ disodium is used as a raw material, and an aqueous solution having an ethanol concentration of 20 to 80% by mass is used, the reaction time needs to be shorter than 12 hours. In this case, when the reaction is performed for a time longer than this (12 hours or more), the crystals 2 are mixed. PQQ monosodium can be produced with the amount of the acid added being an equal amount in the case of PQQ disodium and being moles in a double amount for the PQQ trisodium raw material. In order to quickly form the crystals, an excess amount of the acid should be added, and by allowing a sodium salt, particularly common salt, to coexist at this time, the crystals 1 of PQQ monosodium can be stably removed. The crystals 1 of PQQ monosodium in this embodiment are in a metastable state immediately before forming a free form. Therefore, under these conditions, when the reaction is performed for a long time, crystals comprising no sodium may deposit. Therefore, for crystal making, suitable conditions are preferably selected with time and temperature controlled. The acid that can be used in this embodiment is preferably a strong acid, hydrochloric acid, sulfuric acid, or nitric acid, but the reaction can be similarly caused even with a weak acid. The weak acid that can be used is, for example, acetic acid, lactic acid, formic acid, citric acid, or phosphoric acid. The acid used is not limited, and the reaction should be performed under conditions in which the target crystals are obtained.

In the method for producing the crystals 1 of PQQ monosodium in this embodiment, the step of adding an excess amount of an acid is preferably performed in the presence of common salt.

Here, the amount of common salt is preferably 2 to 250 times, more preferably 5 to 100 times, the mass of pyrroloquinoline quinone disodium and/or pyrroloquinoline quinone trisodium.

The crystals 1 of PQQ monosodium in this embodiment can be obtained, for example, by setting the pH of the aqueous solution at a predetermined value and then performing the reaction for 0.1 to 140 hours. More preferably, the reaction time can be 0.5 to 96 hours. The reaction can be performed at a reaction temperature of 0 to 90° C., more preferably 3 to 60° C. The conditions of crystallization can be freely selected considering the influence of the presence or absence and intensity of stirring on the quality of the formed crystals.

The crystals 2 of PQQ monosodium in this embodiment are formed, for example, by reacting PQQ disodium as a raw material in ethanol-water, or recrystallizing in ethanol-water the crystals 1 once crystallized. For conditions under which the crystals 2 of PQQ monosodium in this embodiment are easier to form, they can be obtained by crystallization in an aqueous solution having an ethanol concentration of 20 to 80% by mass. After these crystals are produced, they can also be recrystallized. The crystals 2 of PQQ monosodium in this embodiment can be obtained, for example, by performing the reaction for 12 to 140 hours. More preferably, the reaction time can be 12 to 90 hours. The reaction can be performed at a reaction temperature of 0 to 90° C., more preferably 40 to 60° C.

The obtained crystals can be obtained by filtration, centrifugation, or decantation. Further, these can also be washed with an alcohol or the like and provided.

Further, in the method for producing the crystals 2 of PQQ monosodium in this embodiment, the step of adding an acid is more preferably performed in the presence of an aqueous solution having an ethanol concentration of 10 to 90% by mass. The ethanol concentration is preferably 15 to 85% by mass, more preferably 20 to 80% by mass, and further preferably 30 to 70% by mass.

The crystals 1 and 2 of PQQ monosodium in this embodiment have high bulk density and are easy to handle. In addition, the crystals 1 and 2 of PQQ monosodium in this embodiment do not undergo change such as gelation even when added to a solution, and therefore solution preparation is easy. In addition, the crystals 2 of PQQ monosodium in this embodiment are low water content crystals and have high bulk density. The PQQ monosodium crystals 1 and 2 in this embodiment further have the advantage of having high purity because they are crystals.

Further, the crystals of PQQ monosodium in this embodiment can be mixed with disodium for the control of solubility, dissolution speed, and color.

The composition in this embodiment comprises both the pyrroloquinoline quinone monosodium in this embodiment and pyrroloquinoline quinone disodium.

In the composition in this embodiment, for the mixing ratio between pyrroloquinoline quinone monosodium and pyrroloquinoline quinone disodium, the pyrroloquinoline quinone monosodium crystal content is preferably 5 to 95% by mass, more preferably 5 to 50% by mass. The composition in this embodiment can also be produced by mixing the crystals, but can also be produced by partially performing crystallization. In other words, mixed crystals of pyrroloquinoline quinone disodium and pyrroloquinoline quinone monosodium can be obtained in the step of adding an excess amount of an acid to pyrroloquinoline quinone disodium and/or pyrroloquinoline quinone trisodium described above.

Therefore, the crystals 1 and 2 of PQQ monosodium in this embodiment can be preferably used for humans or animals as foods, functional foods, nutrients, cosmetics, drugs, or quasi-drugs. The functional foods here mean foods ingested for the purpose of the maintenance of health or nutrition instead of meals, such as health foods, supplements, foods with nutrient function claims, foods with nutrition and health claims, and foods for specified health uses. Examples of specific forms of foods, functional foods, nutrients, cosmetics, drugs, or quasi-drugs include, but are not limited to, capsules (for example, gelatin capsules and soft capsules), tablets, chewables, pills, and drinkable preparations. The crystals 1 and crystals 2 of PQQ monosodium in this embodiment have high bulk density and are therefore advantageous for filling capsules.

In this embodiment, a drug composition, a cosmetic composition, a functional food, and a nutrient comprising the above-described crystals of PQQ monosodium are provided. Particularly the above-described crystals of PQQ monosodium are excellent in penetration into the skin, and therefore the drug composition in this embodiment comprising the above-described crystals of PQQ monosodium can be a drug composition for transdermal administration. In addition, the above-described crystals of PQQ monosodium are excellent in dispersibility in oils and fats and therefore suitable for formulation for oil dispersion-based preparations. Therefore, the drug composition and the cosmetic composition in this embodiment comprising the above-described crystals of PQQ monosodium can be preferably provided in the form of a dispersion preparation such as an emulsion or a suspension, in the form of a semisolid preparation such as an ointment or a cream, or a molded preparation such as a soft capsule.

When the above-described crystals of PQQ monosodium are commercialized as a functional food, for example, a sweetener, a colorant, a preservative, a thickening stabilizer, an antioxidant, a color former, a bleaching agent, an antibacterial and antifungal agent, a gum base, a bittering agent, an enzyme, a brightening agent, an acidulant, a seasoning, an emulsifier, a fortifier, a production agent, a flavor, and a spice extract can be used as additives. The above-described PQQ monosodium crystals can be generally added to usual foods, for example, miso, soy sauce, instant miso soup, ramen, fried noodles, curry, corn soup, mapo tofu, mapo eggplant, pasta sauce, pudding, cake, and bread. The drug composition in this embodiment comprising the above-described crystals of PQQ monosodium may comprise the above-described crystals of PQQ monosodium and at least one or more preparation additives. The cosmetic composition in this embodiment may comprise the above-described crystals of PQQ monosodium and at least one or more cosmetic additives. Those skilled in the art can appropriately select preparation additives and cosmetic additives according to the form of formulation of the drug composition and the cosmetic composition.

EXAMPLES

The present invention will be described in more detail below by Reference Example, Examples, and Comparative Examples, but the present invention is not limited only to these examples.

Powder X-ray diffraction was performed with
X-rays: Cu/tube voltage 40 kV/tube current 100 mA
scan speed: 4.000°/min
sampling width: 0.020°
using RINT 2500 manufactured by Rigaku Corporation.

The measurement of the water content (% by mass) of crystals was performed by the Karl Fischer method.
Method for Measuring Amount of Na For the sodium electrode, HORIBA compact ion meter LAQUAtwin was used.
1 mg of a sample was dissolved in 1 mL of a 0.5% choline hydroxide aqueous solution. This solution was measured by a 200 µL sodium electrode. The lower limit of detection was 1 ppm or less.

Reference Example 1: Raw Material PQQ Trisodium and PQQ Disodium

For PQQ disodium, PQQ disodium manufactured by MITSUBISHI GAS CHEMICAL COMPANY, INC. (trade name: BioPQQ) was used. PQQ trisodium was obtained by salting out at a pH of 6-8 with BioPQQ.

Example 1

Crystal Form 1: Pyrroloquinoline Quinone Monosodium (NaCl Excess and Hydrochloric Acid Excess)

Figure 3:
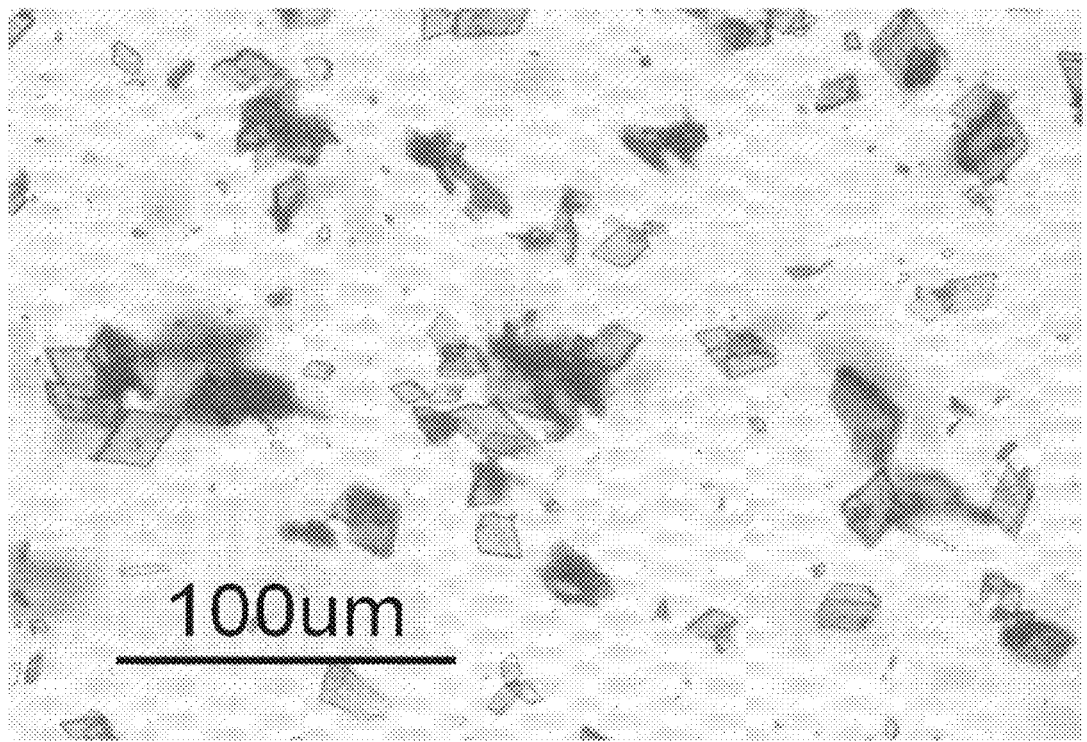
FIG. 3 shows a micrograph of the PQQ monosodium crystals 1 of Example 1.

1.0 g of PQQ disodium was mixed with 2 g of NaCl, 7 mL of concentrated hydrochloric acid, and 1 L of water at 37 degrees. At this time, NaCl and hydrochloric acid were present in the solution in amounts 10 times or more and 30 times or more the amount of PQQ disodium. The solution was stirred for 3 hours followed by centrifugation, 2-propanol washing, and drying to obtain crystals having a mass of 0.72 g. The obtained crystals turned out to be PQQ monosodium from the amount of Na. A micrograph of the obtained crystals of PQQ monosodium is shown in FIG. 3. Further, the results of the powder X-ray diffraction of the obtained crystals of PQQ monosodium are shown in FIG. 4.

The obtained crystals of PQQ monosodium were particles that were quadrangular and had fluidity. These crystals were not in the form of a film even if filtered, and had good dispersibility. The crystallization was performed in a short treatment time.

Figure 4:
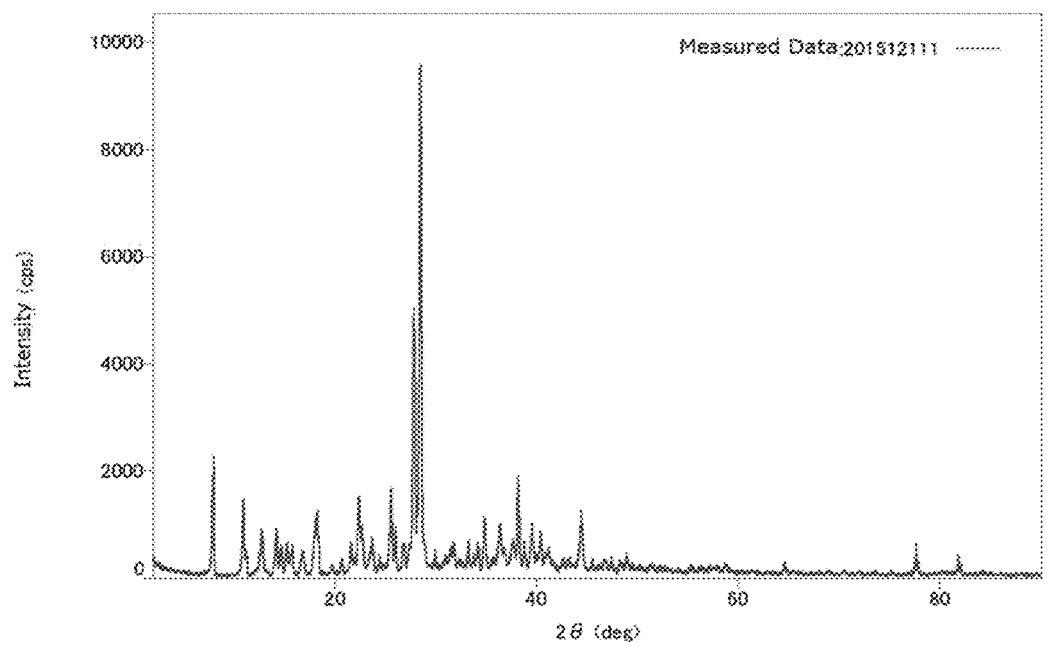
FIG. 4 shows the powder X-ray diffraction of the PQQ monosodium crystals 1 of Example 1.

When powder X-ray diffraction was performed, the obtained crystals were found to be PQQ monosodium crystals showing $2\theta$ angle peaks at 7.9, 10.9, 11.2, 18.4, 22.4, 25.7, 28.0, and 28.8±0.4° (FIG. 4).

The amount of water in the obtained PQQ monosodium was 16.1% by mass.

Example 2: Single Crystal Structure Analysis

In order to determine the atomic arrangement of crystals, single crystal structure analysis was performed. In powder X-ray diffraction (XRD), the peaks of the XYZ axes of crystals are measured in a mixed state, but in single crystal structure analysis, these can be separately measured, and therefore the positions of atoms can be easily determined. The measurement was performed using R-AXIS RAPID Imaging Plate Diffractometer manufactured by Rigaku Corporation.

Figure 5:
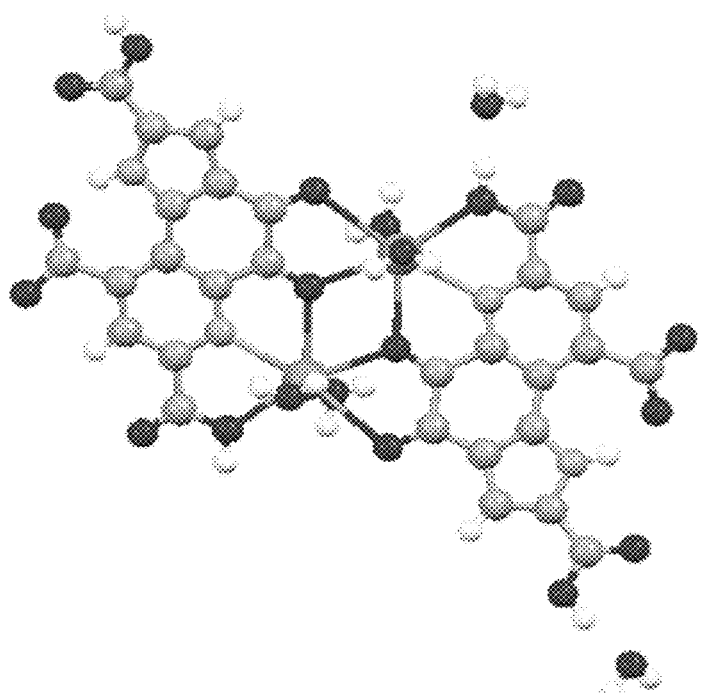
FIG. 5 shows a structure showing the PQQ monosodium crystal of Example 2 with balls and sticks.

50 mg of a disodium salt was added to 15 mL of artificial gastric juice, and the mixture was stirred. The obtained solution was filtered through a 0.2 μm filter, and the filtrate was stored at 4° C. for 1 week. The single crystal structure analysis of one deposited dark red crystal was performed. As a result, it was a monosodium salt having the structure shown in FIG. 5.

This structure had a structure comprising two pyrroloquinoline quinones and two sodiums and comprised four waters of crystallization. Unlike the generally expected structure, sodium was at the position shown in formula (1), and the hydrogen of a carboxylic acid bonded to this sodium was bonded without dissociation.

Figure 6:
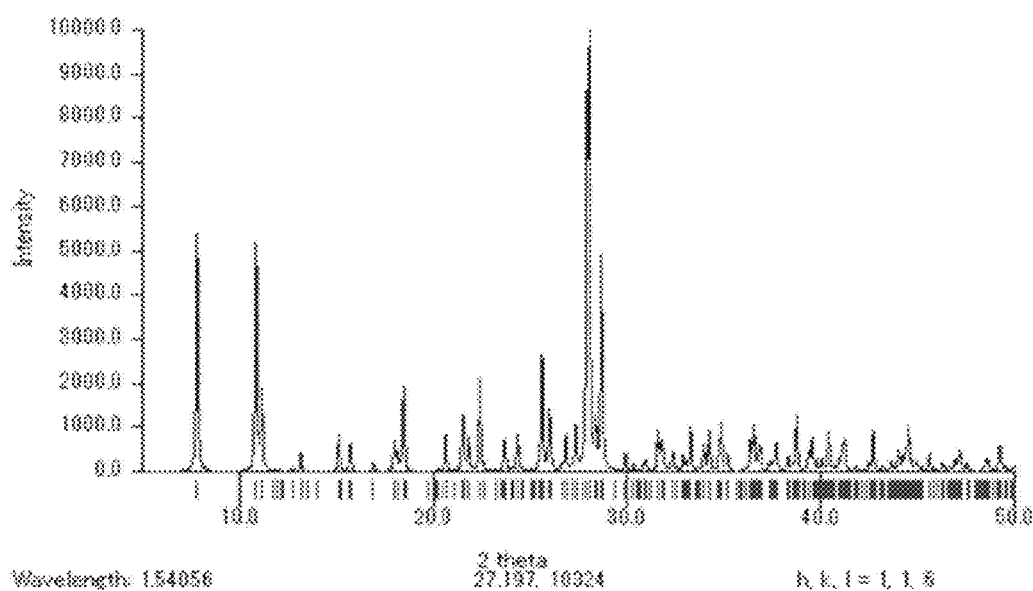
FIG. 6 shows powder X-ray diffraction converted from single crystal data on the PQQ monosodium crystals 1 of Example 2.

Peaks obtained by converting this crystal structure of the monosodium salt into powder X-ray diffraction data by Mercury, which is structure analysis software, are shown in FIG. 6. These peaks match those in Example 1, and it was confirmed that all of crystal structures obtained in the present invention were the same.

Example 3: Crystals 1 High Concentration Charging of Pyrroloquinoline Quinone Disodium 2 g of NaCl and 7 mL of concentrated hydrochloric acid were mixed with 1 L of water. 0.6 g of PQQ disodium was mixed with 40 mL of this solution. The mixture was stirred at 37° C. for 3 hours followed by centrifugation, 2-propanol washing, and drying to obtain crystals having a mass of 0.56 g. The obtained crystals turned out to be PQQ monosodium from the amount of Na. The powder X-ray analysis of the obtained crystals of PQQ monosodium also had the same peaks as Example 1.

Example 4 Crystals 1 High NaCl Concentration 0.50 g of PQQ disodium was mixed with 50 g of NaCl, 500 mL of water, and 3.5 mL of concentrated hydrochloric acid, and the mixture was reacted at 37° C. overnight. The obtained reaction liquid was subjected to centrifugation, 2-propanol washing, and drying to obtain crystals having a mass of 0.41 g. The obtained crystals turned out to be PQQ monosodium from the amount of Na. The powder X-ray analysis of the obtained crystals of PQQ monosodium also had the same peaks as Example 1.

Example 5 Crystals 1 Pyrroloquinoline Quinone Trisodium Raw Material

The pyrroloquinoline quinone trisodium obtained in Reference Example 1 was used. 0.50 g of the PQQ trisodium was mixed with 50 g of NaCl, 500 mL of water, and 3.5 mL of concentrated hydrochloric acid, and the mixture was reacted at 37° C. overnight. The obtained reaction liquid was subjected to centrifugation, 2-propanol washing, and drying to obtain crystals having a mass of 0.32 g. The obtained crystals turned out to be PQQ monosodium from the amount of Na. The powder X-ray analysis of the obtained crystals of PQQ monosodium also had the same peaks as Example 1.

Example 6 Crystals 1 Sample Having High Bulk Specific Gravity 2 g of PQQ trisodium, 25 mL of ethanol, 20 mL of water, and 5 mL of 2 N hydrochloric acid were stirred at room temperature for 1 hour and then reacted at 50° C. for 5 days. The obtained reaction liquid was subjected to centrifugation, 2-propanol washing, and drying to obtain crystals having a mass of 1.46 g. For the obtained crystals, the powder X-ray analysis of the obtained crystals of PQQ monosodium also had the same peaks as Example 1. The amount of water in the obtained PQQ monosodium was 15.7% by mass.

Figure 7:
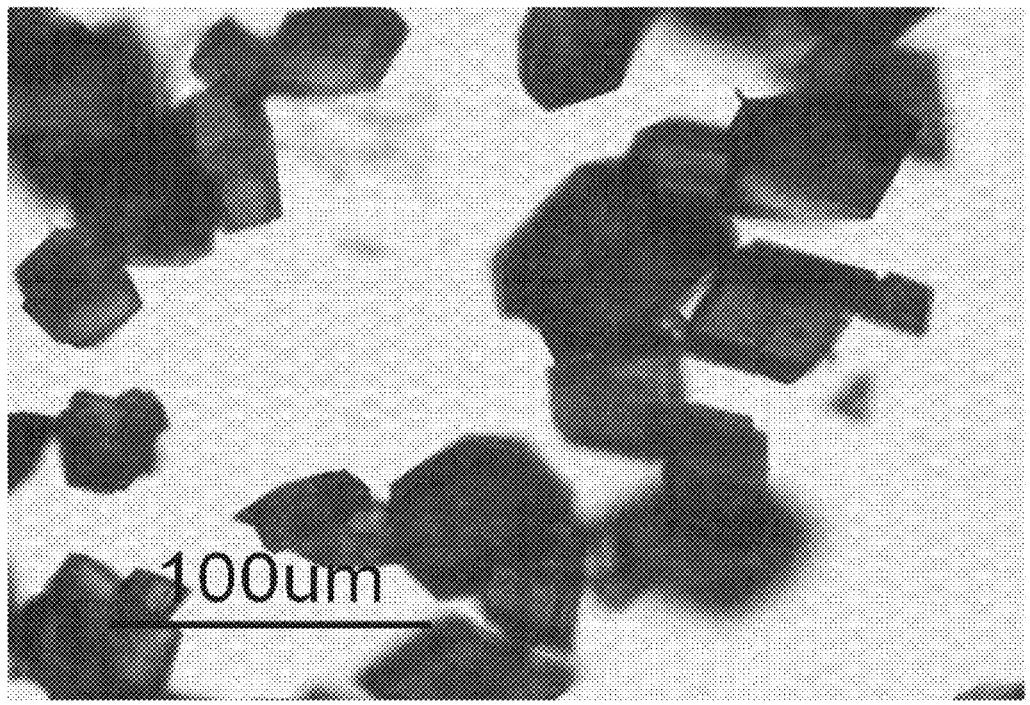
FIG. 7 shows a micrograph of the PQQ monosodium crystals 1 having high bulk density in Example 6.

A micrograph of the obtained PQQ monosodium is shown in FIG. 7.

The crystals became large, and thus the bulk density increased. The fluidity was also very good compared with small crystals.

Example 7 Crystals 2

2 g of pyrroloquinoline quinone disodium was added to a mixed liquid of 25 mL of ethanol and 22.5 mL of water. 2.5 mL of 2 N hydrochloric acid was added thereto, and the mixture was stirred at room temperature for 1 hour. This suspension was heated to 50° C. to obtain a sample. After 5 days, the sample was filtered and then dried under reduced pressure to obtain crystals having a mass of 1.71 g. The obtained crystals turned out to be PQQ monosodium from the amount of Na.

Figure 8:
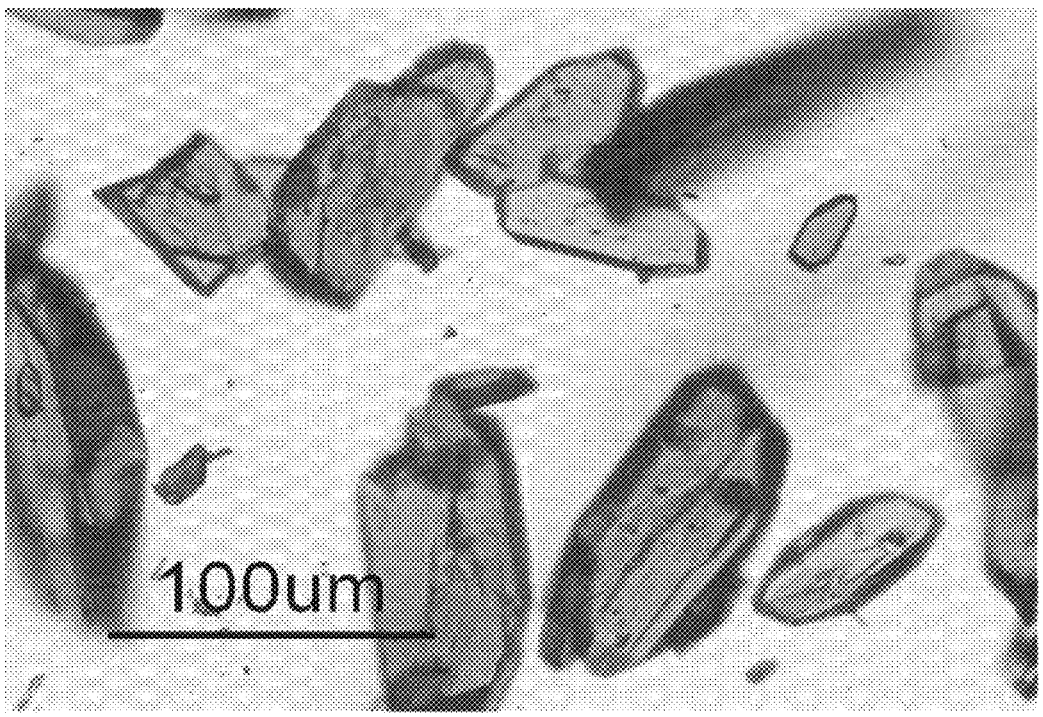
FIG. 8 shows a micrograph of the PQQ monosodium crystals 2 of Example 7.

A micrograph of the obtained PQQ monosodium is shown in FIG. 8. The results of the powder X-ray analysis of the obtained PQQ monosodium are shown in FIG. 9.

The amount of water in the obtained PQQ monosodium was 5.0% by mass. The amount of water in the crystals was small.

The single crystal structure analysis of the crystal 2 was performed as in Example 2. As a result, it was a monosodium salt having the structure shown in FIG. 10.

Comparative Example 1: Reaction of PQQ Disodium and Only Hydrochloric Acid (Conditions without Common Salt)

1.0 g of PQQ disodium was mixed with 7 mL of concentrated hydrochloric acid and 1 L of water at 37 degrees. At this time, hydrochloric acid was present in the solution in an amount 30 times or more the amount of PQQ disodium. The obtained solution was stirred for 3 hours followed by centrifugation, 2-propanol washing, and drying to obtain crystals having a mass of 0.71 g. No amount of Na was included in the obtained crystals. Under these conditions, the obtained crystals turned out to be of a PQQ free form. It was found that unless sodium ions, a characteristic of the production of the present invention, were added in an excess amount, sodium came off crystals and monosodium could not be formed in some cases.

Comparative Example 2

Experiment Based on Contents Described in Chinese Laid-Open Application Publication (CN101885725A)

Figure 11:
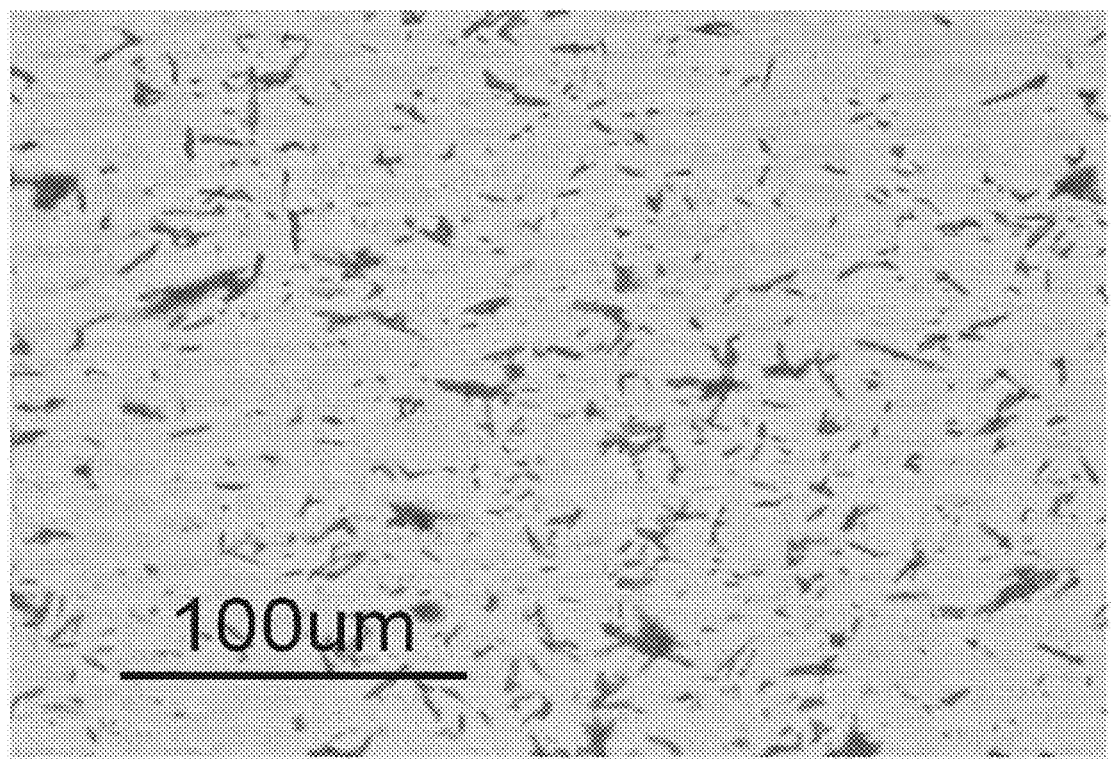
FIG. 11 shows a micrograph of the PQQ monosodium of Comparative Example 2.

2 g of a pyrroloquinoline quinone disodium salt was added to 198 g of water to obtain a disodium salt aqueous solution. The obtained solution was adjusted at a pH of 9 with NaOH. Next, 7.7 g of a liquid obtained by 50%-diluting concentrated hydrochloric acid manufactured by Wako Pure Chemical Industries, Ltd. with water was added to this solution with stirring to set the pH at 0.9. The obtained solution was stirred for 30 minutes, and then the deposited solid was filtered and washed with water and isopropanol. The solid was dried under reduced pressure at 50° C. overnight. The mass of the recovered red crystals was 1.6 g. According to Na analysis, it was found that the obtained crystals had a Na content of 0 and contained no sodium, and were of a PQQ free form. The PQQ free form obtained by this method was used as a raw material. The PQQ free form was dissolved in tetrahydrofuran, and the solution was mixed with a sodium hydroxide aqueous solution.
A micrograph of the obtained crystals is shown in FIG. 11.

The obtained monosodium salt comprised an elongated fibrous solid unlike the Examples. Further, the obtained monosodium salt was very small, and the filtered solid was in the form of a film. The amount of water in the obtained monosodium salt was 16.6% by mass. For example, the structure of the monosodium salt described in Patent Literature 2 was as follows.

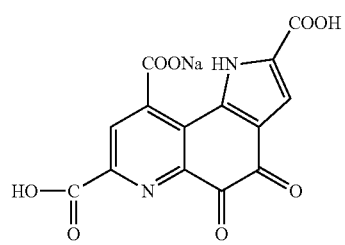

Bulk Density Measurement

Bulk density was measured using a 10 mL volumetric flask. The results are shown in Table 1.

TABLE 1

Bulk Density of Crystals

| | Crystals | Bulk specific gravity (g/ML) |
|---|---|---|
| Example 1 | Crystals 1 | 0.29 |
| Example 3 | Crystals 1 | 0.28 |
| Example 4 | Crystals 1 | 0.52 |
| Example 7 | Crystals 2 | 0.27 |
| Comparative Example 2 | Fibrous | 0.20 |

The bulk specific gravity of the crystals of the Examples is high, and a capsule can be made small at the same mass. An advantage of the fact that a small capsule can be used is that it is easy to swallow and can decrease the burden on the user.

Suspension Fluidity Test

Crystals were mixed with water so as to obtain a concentration of 100 g/L. After mixing at room temperature, the state was observed at 4° C.

TABLE 2

Fluidity When Crystals Are Added to Water

| | Crystals | Fluidity |
|---|---|---|
| Example 1 | Crystals 1 | Yes |
| Example 4 | Crystals 1 | Yes |

TABLE 2-continued

Fluidity When Crystals Are Added to Water

| | Crystals | Fluidity |
|---|---|---|
| Example 7 | Crystals 2 | Yes |
| Comparative Example 2 | Fibrous | No |

It was found that the crystals of the Examples had fluidity even in a thick state. An advantage of this is that the crystals of the Examples can be provided as a thick solution in a process in solution preparation. The substance of Comparative Example 2 has no fluidity and is difficult to use in the process of preparing it in a solution.

Examples 8 to 14

Solubility and Color of Mixtures

As monosodium crystals 1, those formed in Example 1 were used, and as monosodium crystals 2, those formed in Example 7 were used. Powders were mixed in a proportion shown in Table 3, and the color of the powder was recorded. 1 mL of water was added to a crystal mass of 10 mg at room temperature. The obtained aqueous solution was subjected to ultrasonic waves for 5 minutes, warmed with hot water at 70 degrees for 10 minutes, and then cooled with water at room temperature for 30 minutes. The aqueous solution after the cooling was centrifuged, and the supernatant liquid was removed. This was diluted with a phosphate buffer, and the solubility was calculated from absorbance at 330 nm. The results are shown in Table 3.

TABLE 3

Color and Solubility in Form of Powder

| | | | | Color | Solubility mmol/L |
|---|---|---|---|---|---|
| Example 1 | Monosodium crystals 1 | | | Deep red | 4.5 |
| Example 7 | Monosodium crystals 2 | | | Black | 2.1 |
| Raw material | Disodium | | | Red | 7.5 |
| Example 8 | Monosodium crystals 1 | 10% | | Red | 7.0 |
| | Disodium | 90% | | | |
| Example 10 | Monosodium crystals 1 | 50% | | Deep red | 6.9 |
| | Disodium | 50% | | | |
| Example 11 | Monosodium crystals 1 | 90% | | Dark red | 3.9 |
| | Disodium | 10% | | | |
| Example 12 | Monosodium crystals 2 | 10% | | Dark red | 6.6 |
| | Disodium | 90% | | | |
| Example 13 | Monosodium crystals 2 | 50% | | Dark red | 6.1 |
| | Disodium | 50% | | | |
| Example 14 | Monosodium crystals 1 | 50% | | Dark red | 2.7 |
| | Monosodium crystals 2 | 50% | | | |

By the mixtures of the Examples, it was found that color and solubility were freely set. In addition, it was found that color and solubility were also changed by mixing the same monosodium having different crystal forms. The control of solubility can change absorbency and interaction with food components, and therefore it was found that the mixtures of the Examples were excellent. It was found that the mixtures of the Examples were easy to use in cosmetic and food applications where color was regarded as important.

Example 15 Production of Mixture of Monosodium Crystals and Disodium 2 g of PQQ disodium was mixed with 25 g of ethanol and 23 g of water. 2 mL of 2 N hydrochloric acid was added thereto. The mixture was stirred at room temperature for 2 hours and left at 50 degrees for 18 hours without stirring. The mixture was filtered, washed with ethanol, and dried under reduced pressure. A dark brown solid was obtained. In the obtained solid, the proportion of sodium was 1.5. As a result of optical microscope observation, the obtained solid was a mixture in which PQQ monosodium crystals 2 were contained.

Example 16: Capsules

Hydroxypropylmethyl cellulose capsules #0 sold by GREAT & GRAND Co., Ltd. were used. The capsule was filled with 20 mg of a sample of the crystals obtained in each of the above Examples and Comparative Examples.

The crystals 1 and the crystals 2 were placed in the capsules as they were. The solid of Comparative Example 2 had high bulk and could not be directly placed. The capsule was filled with the solid of Comparative Example 2 by grinding it in a mortar.

The crystals of the Examples were introduced into the capsules without the operation of crushing the solid, and were crystals suitable regarding the use of hard capsules.

Example 17 Thermal Stability Test (70° C. Color Change Test)

1 mg of the crystals obtained in each of Examples 1 and 6 and Comparative Example 2 were placed in a 70° C. oven, and a change in color after 2 hours was observed. The results are shown in Table 4.

TABLE 4

|  | Crystals | Change in color after 2 hours at 70° C. |
| --- | --- | --- |
| Example 1 | Crystals 1 | No change |
| Example 7 | Crystals 2 | No change |
| Comparative Example 2 | Fibrous | Change to black |

The crystals 1 and 2 of the Examples did not change color and were stable even at 70° C.

Example 18 Thermal Stability Test (Solubility Change at 180° C. for 10 Minutes)

Whether the solubility of crystals changed by heat treatment was tested.

1 mg of the crystals obtained in each of Examples 1 and 6 and Comparative Example 2 were sandwiched between cover glasses made of glass, and heated on a hot plate at 180° C. for 10 minutes. Then, the crystals were mixed with 10 mL of water, and the mixture was stirred for 15 minutes. At this time, the state was recorded. The aqueous solution after the stirring was filtered through a 0.5 μm filter and diluted to 1/10, and absorbance at 330 nm was measured. A change in the solubility of the crystals before and after the heat treatment was examined by this measurement. The solubility after the heating is shown in Table 5 with the solubility of the crystals before the heating being 100.

TABLE 5

|  | Crystals | Before heat treatment | State of dissolution after heating at 180° C. for 10 minutes | State of dissolution after heating at 180° C. for 10 minutes (with 100 before heating) |
| --- | --- | --- | --- | --- |
| Example 1 | Crystals 1 | All dissolve | All dissolve | 82 |
| Example 7 | Crystals 2 | All dissolve | All dissolve | 100 |
| Comparative Example 2 | Fibrous | All dissolve | Amount of precipitate is large | 71 |

All crystals used in the experiment dissolved in water before the heat treatment. When the heat treatment was performed, the amount of the poorly soluble component increased, and the quality changed. The crystals 2 were particularly stable, and there was no change in solubility. For the crystals 2, no precipitate is seen in appearance, but the absorbance decreases, and it is thought that the crystals 2 are minute insoluble crystals. Compared with the fibrous form, the change was small. For the fibrous form of the Comparative Example, the insoluble component appeared and was seen as a precipitate. In addition, also from the absorbance, it was clear that the amount of the insoluble component was large.

The crystals 1 and 2 of the Examples were stable even at high temperature used in food processing. For the conventional ones, a precipitate formed, and the quality changed.

Example 19 Reaction with Powdered Green Tea 2 mg of powdered green tea and 1 mg of the crystals obtained in each of Examples 1 and 6 and Comparative Example 2 were mixed. As a model in which the mixed powder was wet, 100 μL of water was added. For the crystals 2, the tea leaves did not change color. However, for the crystals 1 and the fibrous form (Comparative Example 2), the tea leaves changed color to orange. The crystals 2 were very stable and excellent in powder mixing.

Example 20 Test of Penetration into Skin

The skin of a pig was washed with tap water, and the water was completely wiped off. 5 mg of one of crystals was brought into contact with this skin of the pig and then fixed to the skin by wrapping in plastic wrap. After 80 minutes at 37° C., the tape was peeled, and the skin was washed with tap water to remove the test composition adhering to the skin surface. Evaluation was performed by capturing an image of the test composition by a scanner and measuring a change in the brightness of the skin using image software (product name: Paint (software included with Windows (registered trademark) XP, manufactured by Microsoft Corporation). At this time, the change in the brightness of the skin was calculated by

[[brightness of untreated skin−brightness after treatment]/[brightness of untreated skin]]×100.

TABLE 6

|  | Crystals | Penetration |
| --- | --- | --- |
| Example 1 | Crystals 1 | 8.4 |
| Example 7 | Crystals 2 | 4.3 |
| Comparative Example 2 | Fibrous | 1.6 |

The crystals of the Examples were excellent in penetration into the skin and suitable for use in cosmetic applications.

This application is based on Japanese Patent Application No. 2016-128941 filed with the Japan Patent Office on Jun. 29, 2016, the contents of which are incorporated herein by reference.

The invention claimed is:

1. Pyrroloquinoline quinone monosodium having a structure shown in FIG. 10,
    wherein the pyrroloquinoline quinone monosodium is a crystal and showing 2θ angle peaks at 9.9, 16.1, 16.8, and 28.1, each ±0.4°, in powder X-ray diffraction using Cu Kα radiation as shown in FIG. 9.
2. A composition comprising
    (i) the pyrroloquinoline quinone monosodium according to claim 1, and
    (ii) pyrroloquinoline quinone disodium.

* * * * *